United States Patent
Muskett

(10) Patent No.: US 6,458,996 B1
(45) Date of Patent: Oct. 1, 2002

(54) PROCESS FOR THE PRODUCTION OF ACETIC ACID

(75) Inventor: Michael James Muskett, Beverley (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/357,170

(22) Filed: Jul. 19, 1999

(30) Foreign Application Priority Data

Jul. 29, 1998 (GB) .............................................. 9816385

(51) Int. Cl.$^7$ .............................................. C07C 51/21
(52) U.S. Cl. ...................................................... 562/536
(58) Field of Search .......................................... 562/536

(56) References Cited

U.S. PATENT DOCUMENTS

| | | | |
|---|---|---|---|
| 3,769,177 A | 10/1973 | Eubanks et al. | |
| 3,772,380 A | 11/1973 | Paulik et al. | |
| 4,039,395 A | 8/1977 | Eby | |
| 4,102,922 A | 7/1978 | Price | |

FOREIGN PATENT DOCUMENTS

| | | |
|---|---|---|
| DE | 17 67 150 | 5/1972 |
| EP | 0 087 870 A1 | 2/1983 |
| EP | 0 573 189 A1 | 5/1993 |
| EP | 0 573 189 A1 * | 12/1993 |
| EP | 0 616 997 A1 | 3/1994 |
| EP | 0 618 183 A1 | 3/1994 |
| EP | 0 618 184 A1 | 3/1994 |
| EP | 0 616 997 A1 * | 9/1994 |
| EP | 0 657 386 A1 | 12/1994 |
| EP | 0 768 295 A1 | 4/1996 |
| EP | 0 768 295 A1 | 4/1997 |
| GB | 1 234 121 | 1/1969 |
| GB | 1 468 940 | 9/1974 |
| GB | 1 538 783 | 3/1976 |
| WO | WO 96/31456 | 10/1996 |
| WO | 98/22420 | 5/1998 |

OTHER PUBLICATIONS

Catalysis Today, 18 (1993) pp 325–354, Elsevier Science Publisher B.V., Amsterdam, Howard, M.J. et al.; "$C_1$ to acetyls: catalysis and process".

* cited by examiner

Primary Examiner—Gary Geist
Assistant Examiner—Robert W Deemie
(74) Attorney, Agent, or Firm—Nixon & Vanderhye

(57) ABSTRACT

In a process for the production of acetic acid by carbonylation of methanol and/or a reactive derivative in the presence of a Group VIII noble metal carbonylation catalyst, methyl iodide co-catalyst at a concentration of at least 2 wt %, optionally at least one promoter at least a finite concentration of water, methyl acetate at a concentration of at least 8% w/w and acetic acid product, the separability of an upper (aqueous) layer and a lower (organic) layer in the decanter of the light ends column is achieved by maintaining the concentration of acetic acid in the condensed overhead vapor fraction passed to the decanter at or below 8 wt %.

17 Claims, 2 Drawing Sheets

PROCESS FOR THE PRODUCTION OF ACETIC ACID

BACKGROUND OF THE INVENTION

The present invention relates to a process for the production of acetic acid by the carbonylation of methanol and/or a reactive derivative thereof in the presence of a Group VIII noble metal catalyst and a hydrocarbyl halide co-catalyst.

Processes for producing acetic acid by the Group VIII noble metal catalysed, hydrocarbyl halide co-catalysed carbonylation of alcohols and/or their reactive derivatives are well-known in the art. Representative of such art employing rhodium as the Group VIII noble metal catalyst may be mentioned, for example, U.S. Pat. No. 3,772,380; GB-A-1468940; GB-A-1538783 and EP-A-0087070. Representative of such art using iridium as the Group VIII noble metal catalyst may be mentioned, for example, GB-A-1,234,121; U.S. Pat. No. 3,772,380; DE-A-1767150; EP-A-0616997; EP-A-0618184; EP-A-0618183; and EP-A-0657386.

In continuous liquid phase processes for the production of acetic acid by the carbonylation of methanol and/or a reactive derivative thereof in the presence of a Group VIII noble metal the acetic acid product is recovered from the liquid reaction composition and dried; the remaining components of the reaction composition being recycled to the reactor to maintain their concentration therein.

Howard et al in Catalysis Today, 18(1993), 325–354 describe the rhodium and iridium catalysed carbonylation of methanol to acetic acid. The continuous rhodium-catalysed, homogeneous methanol carbonylation process is said to consist of three basic sections; reaction, purification and off-gas treatment. The reaction section comprises a stirred tank reactor, operated at elevated temperature and pressure, and a flash vessel. Liquid reaction composition is withdrawn from the reactor and is passed through a flashing valve to the flash tank where the majority of the lighter components of the liquid reaction composition (methyl iodide, methyl acetate and water) together with product acetic acid are vapourised. The vapour fraction is then passed to the purification section whilst the liquid fraction (comprising the rhodium catalyst in acetic acid) is recycled to the reactor (as shown in FIG. 2 of Howard et al). The purification section is said to comprise a first distillation column (the light ends column), a second distillation column (the drying column) and a third distillation column (the heavy ends column) (as shown in FIG. 3 of Howard et al). In the lights ends column methyl iodide and methyl acetate are removed overhead along with some water and acetic acid. The vapour is condensed and allowed to separate into two phases in a decanter, both phases being returned to the reactor. Wet acetic acid is removed from the light ends column typically as a side draw and is fed to the drying column where water is removed overhead and an essentially dry acetic acid stream is removed from the base of the distillation zone. From FIG. 3 of Howard et al it can be seen that the overhead water stream from the drying column is recycled to the reaction section. Heavy liquid by-products are removed from the base of the heavy ends column with product acetic acid being taken as a side stream.

In practice the upper (aqueous layer) from the decanter, in whole or in part, is returned to the light ends column as reflux and the lower (organic layer) from the decanter is recycled to the reactor. For operational reasons it is highly desirable that two separable phases are maintained in the decanter. Decanter stability is of paramount importance in the successful operation of the continuous carbonylation process. If the decanter becomes single phase, the resulting composition change tends to increase the water content in the reactor, which in turn has a significant impact on reaction activity for iridium catalysed carbonylation.

EP-A-0768295 describes one method of maintaining two separable phases in the reactor in circumstances such that the concentration of water contained in the carbonylation liquid reaction composition decreases or the concentration of methyl acetate contained in the liquid reaction composition increases. Thus EP-A-0768295 discloses a process for producing acetic acid by reacting continuously at least one selected from methanol, methyl acetate and dimethyl ether with carbon monoxide in the presence of a Group VIII metal-containing catalyst, methyl iodide and water, comprising (a) a step in which a crude reaction liquid is withdrawn from a carbonylation step and introduced into a flash zone, and a catalyst circulating liquid containing a catalyst component which is not evaporated in the flash zone is circulated into a carbonylation reactor, (b) a step in which a vapour fraction evaporated in the flash zone is fed into a first distillation column in the form of a vapour or a liquid, (c) a step in which a low boiling circulating stream comprising water, methyl acetate, methyl iodide and acetic acid is withdrawn from the top of the first distillation column, and (d) a step in which crude acetic acid is withdrawn from the bottom or the side cut near the bottom of the first distillation column, characterised in that a liquid separation state in the decanter at the top of the first distillation column is maintained by adding water to the first distillation column, lowering the cooling temperature at the overhead part of the first distillation column, or reducing the concentration of methyl acetate contained in the liquid fed into the decanter at the top of the first distillation column.

EP-A-0768295 teaches that when two phases do not form in the decanter liquid and the unseparated liquid is recycled to the reactor, by-product carbonyl compounds, such as acetaldehyde, crotonaldehyde and 2-ethylcrotonaldehyde, and organic iodine compounds such as hexyl iodide, build up to an unacceptable level in the product acetic acid.

European patent publication number EP-0573189-A1 describes a process for the production of acetic acid by carbonylation of methanol in the presence of a rhodium carbonylation catalyst. The methyl acetate concentration in the liquid reaction composition is said to be at least 2% by weight, preferably in the range 2% to 15% by weight more preferably in the range 3% to 10% by weight. Whilst in Examples 4 and 5 the combined overhead streams forming the light ends recycles shown were calculated to have 0.96% and 1.33% by weight acetic acid, the methyl acetate concentrations in the reactors were only 3.1% and 7.3% by weight.

DESCRIPTION OF THE INVENTION

We have found that at high methyl acetate concentrations, typically 8% w/w or greater in the liquid reaction composition in the carbonylation reactor, particularly at low levels of water and methyl iodide, which conditions are typically associated with the use of iridium as the carbonylation catalyst, it becomes increasingly difficult to achieve two separable phases in the decanter, which in turn may give rise to product quality problems of the type referred to in EP-A-0768295, and plant capacity problems, largely as a result of hydraulic limitations to both control valves and pumps.

We have found that a solution to the problem of maintaining two liquid phases in a continuously operated decanter is to control the concentration of acetic acid in the overhead fraction fed from the light ends column to the decanter. EP-A-0768295 makes no mention of acetic acid concentration in the overhead fraction and its impact on the maintenance of two phases. In off-line experiments we have found that a typical decanter feed will form a single phase with about 14% w/w or more of acetic acid present. However, in a continuously operated decanter, even lower levels of acetic acid must be achieved (8 wt % or lower) in order to maintain stable operation. This is due to the increasing water content of the organic phase, which depletes the light ends column overheads of water by recycling it directly back to the reactor. This causes the water concentration to fall and the phase separation to become more difficult. A feed-back mechanism then becomes dominant and the decanter becomes single phase.

Accordingly the present invention provides a continuous process for the production of acetic acid by the carbonylation of methanol and/or a reactive derivative thereof which process comprises the steps of:

(I) feeding methanol and/or a reactive derivative thereof to a carbonylation reactor in which the methanol and/or reactive derivative thereof is reacted with carbon monoxide in a liquid reaction composition, the liquid reaction composition comprising a Group VIII noble metal carbonylation catalyst, methyl iodide co-catalyst at a concentration of at least 2% w/w, optionally at least one promoter, at least a finite concentration of water, methyl acetate at a concentration of at least 8% w/w and acetic acid product;

(II) withdrawing liquid reaction composition from the carbonylation reactor and introducing the withdrawn liquid reaction composition into at least one flash separation zone, with or without the addition of heat, to produce a vapour fraction comprising water, acetic acid product, methyl acetate and methyl iodide, and a liquid fraction comprising Group VIII noble metal carbonylation catalyst and optionally at least one promoter;

(III) recycling the liquid fraction from step (II) to the carbonylation reactor;

(IV) introducing the vapour fraction from step (II) into a light ends distillation column;

(V) removing a process stream comprising acetic acid product from the light ends distillation column;

(VI) removing from the head of the light ends distillation column a vapour fraction comprising methyl acetate, methyl iodide, water and acetic acid;

(VII) condensing the overhead vapour fraction from (VI);

(VIII) passing the condensed overhead vapour fraction from (VII) to a decanter wherein the fraction is separated into an upper (aqueous) layer and a lower (organic) layer;

(IX) recycling in whole or in part the upper (aqueous) layer separated in (VIII) as reflux to the light ends distillation column and the lower (organic) layer separated in (VIII) in whole or in part to the reactor characterised in that separability of an upper (aqueous) layer and a lower (organic) layer in the decanter in step (VIII) is achieved by maintaining the concentration of acetic acid in the condensed overhead vapour fraction passed to the decanter at or below 8 wt %.

The concentration of acetic acid in the condensed vapour fraction passed to the decanter is preferably maintained below 8 wt %, preferably below 6 wt %, more preferably less than 5 wt %. Maintenance of the concentration of acetic acid in the condensed vapour fraction within the aforesaid ranges is largely achievable by suitable operation of the light ends distillation column. Thus, the reflux ratio within the column and/or the number of theoretical stages in the column are selected such that the acetic acid concentration in the condensed vapour fraction is 8 wt %, or below. Typically, the light ends column contains a relatively small number of stages (around 10 in total). It has been found that the aqueous phase must all be refluxed to the column to maintain two liquid phases in practice in a commercial unit operating with about 10 theoretical stages above the feed. It is preferred that the light ends column has greater than 10, more preferably 15, or greater, theoretical stages above the feed. Increasing the number of theoretical stages allows lower reflux ratios to be employed, which gives a benefit in terms of water removal efficiency and thus reduced purification costs. Another modification by which the acetic acid concentration in the decanter may be maintained within the aforesaid limits is to relocate any recycle streams having a substantial acetic acid content, which otherwise may formerly have been fed to the condenser and thus directly into the decanter, to the light ends distillation column, suitably at a point close to the feed point of the vapour fraction from step (II) so as to allow the acetic acid in the recycle stream to be separated out from this stream by the stages above the feed. Such a recycle stream may be, for example, a vapour return stream from the off-gas treatment section of the process.

As regards the decanter itself, a conventional design for methanol carbonylation plants includes the provision of a boot, which takes the form of a short vertical cylindrical section depending from the horizontal cylindrical section. This is a standard design feature for systems where there is either a low volume flow of heavy phase, or where the heavy phase density is very high and it is desirable to minimise the inventory of heavy phase material. It has been found that under the relatively high methyl acetate concentration conditions prevailing in the process of the present invention it is possible to eliminate the boot normally present in the construction of the decanter. Elimination of the boot from the decanter provides the advantage of capital cost savings due to simpler fabrication of the decanter vessel. It also avoids the possibility of poorer separation caused by turbulence within the boot induced by high volume flows.

It is further preferred that the decanter contains plate pack separators, which are commercially available (from, for example Natco, Tulsa, Okla.), to enhance the rate of phase separation. Plate pack separators generally comprise stacks of inclined, corrugated plates which induce coalescence and reduce the residence time required in the decanter. Installation of plate pack separators has the advantage that it facilitates the use of smaller decanters. In turn this leads to the advantage that if the decanter becomes single phase, the disadvantageous impact of increased water content in the reactor referred to hereinabove is minimised.

In step (I) of the process of the present invention methanol and/or a reactive derivative thereof is fed to a carbonylation reactor. Suitable reactive derivatives of methanol include methyl acetate and dimethyl ether.

The methanol and/or reactive derivative thereof is reacted in the carbonylation reactor with carbon monoxide in a liquid reaction composition. The carbon monoxide may be essentially pure or may contain inert impurities such as carbon dioxide, methane, nitrogen, noble gases, water, and $C_1$ to $C_4$ paraffinic hydrocarbons. The presence of hydrogen in the carbon monoxide feed and generated in situ by the water gas shift reaction is preferably kept low as its presence may result in the formation of hydrogenation products. Thus, the amount of hydrogen in the carbon monoxide reactant is preferably less than 1 mol %, more preferably less than 0.5 mol % and yet more preferably less than 0.3 mol % and/or the partial pressure of hydrogen in the carbonylation reactor is preferably less than 1 bar partial pressure, more preferably less than 0.5 bar and yet more preferably less than 0.3 bar. The partial pressure of carbon monoxide in the reactor is suitably in the range greater than 0 to 40 bar, typically from 4 to 30 bar.

The liquid reaction composition in the reactor comprises a Group VIII noble metal carbonylation catalyst, methyl iodide co-catalyst optionally at least one promoter, at least a finite concentration of water, methyl acetate at a concentration of at least 8% w/w and acetic acid product.

Of the Group VIII noble metals rhodium and iridium are preferred. The noble metal catalyst may comprise any metal-containing compound which is soluble in the liquid reaction composition. The metal catalyst may be added to the liquid reaction composition in any suitable form which dissolves in the liquid reaction composition or is convertible therein to a soluble form. Suitable compounds are described in the aforesaid patent publications relating to iridium—and rhodium catalysed carbonylations. Typically carbonyl complexes, halide salts and acetate salts of the metals may be employed. Rhodium may be present in an amount of from 50 to 5000 ppm, preferably from 100 to 1500 ppm. Iridium may be present in an amount in the range from 100 to 6000 ppm, preferably from 400 to 3000 ppm.

As co-catalyst there is used methyl iodide. Methyl iodide may suitably be present in the liquid reaction composition in an amount in the range from 2 to 20%, preferably from 4 to 16% by weight.

The choice of promoter when present in the liquid reaction composition depends to some extent on the nature of the Group VIII noble metal catalyst. When iridium is employed as the carbonylation catalyst the optional promoter is suitably a metal selected from the group consisting of ruthenium, osmium, cadmium, rhenium, mercury, gallium, indium, tungsten, and mixtures thereof, preferably ruthenium or osmium. Suitably the molar ratio of promoter:iridium is in the range [0.5 to 15]:1. When rhodium is employed as the carbonylation catalyst the optional promoter is suitably selected from the group consisting of iodide salts of alkali and alkaline earth metals, for example lithium iodide, quaternary ammonium iodides, and quaternary phosphonium iodides. Suitably the optional promoter may be present up to its limit of solubility.

Irrespective of the Group VIII noble metal used as carbonylation catalyst the liquid reaction composition in the carbonylation reactor contains at least a finite concentration of water. However, the amounts of water may vary depending on the Group VIII noble metal employed as catalyst. Generally, for rhodium water may be present in an amount in the range from 0.1 to 30%, preferably from 1 to 15% by weight. For iridium water may be present in an amount from 0.1 to 10%, preferably from 1 to 6.5% by weight.

Methyl acetate, irrespective of whether or not it is fed to the carbonylation reactor, is inevitably present in the liquid reaction composition by reason of the reaction of methanol and/or a reactive derivative thereof with acetic acid present as the carbonylation product and/or carbonylation solvent. Insofar as the present invention is concerned methyl acetate is present in the liquid reaction composition in an amount of 8 wt % or greater, typically 8 to 50 wt %, preferably 8 to 35 wt %. Generally, these methyl acetate concentration ranges are those associated with iridium as the Group VIII noble metal catalyst, the methyl acetate concentration using rhodium as catalyst generally, but not necessarily, being at the most 5 wt %, typically below about 3 wt %.

The remainder of the liquid reaction composition comprises acetic acid.

The carbonylation reaction temperature is suitably in the range from 100 to 300° C., preferably in the range from 150 to 220° C. The total pressure in the carbonylation reactor is suitably in the range from 10 to 200 barg, preferably 15 to 100 barg, more preferably 15 to 50 barg.

In step (II) of the process of the present invention liquid reaction composition is withdrawn from the carboniylation reactor and introduced into at least one flash separation zone, with or without the addition of heat, to produce a vapour fraction comprising water, acetic acid product, methyl acetate and methyl iodide, and a liquid fraction comprising Group VIII noble metal carbonylation catalyst and optionally at least one promoter. If a single stage flash is used the pressure may be in the range 0 to 3 barg, with a temperature suitably in the range 100 to 150° C. Using a two-stage flash, the pressure in the first flash may be in the range 1 to 10 barg and the pressure in the second flash may suitably be in the range 0 to 5 barg.

In step (III) of the process the liquid fraction recovered from the flash separation zone in step (II) is recycled to the carbonylation reactor.

In step (IV) of the process the vapour fraction recovered from the flash separation zone in step (II) is introduced into a light ends distillation column. Suitably, the light ends distillation column has up to 40 theoretical stages. The column may be operated at any suitable pressure, for example a heads pressure of about 1.2 barg and a base pressure of about 1.5 barg. The operating temperature of the light ends distillation column will depend upon a number of factors, including the composition of the feed, heads and base streams and the operating pressure. Typical base temperatures may be in the range 125 to 140° C. and typical head temperatures may be in the range 105 to 115° C.

In step (V) of the process a stream comprising acetic acid product is removed from the light ends distillation column. The process stream may be removed at any suitable point, for example above or below the feed point, or as a liquid or vapour from the base of the column. The process stream comprising acetic acid product removed from the light ends distillation column may then be dried, for example, in a drying distillation column, the separated water suitably being either recycled to the carbonylation reactor or removed from the process. The dried acetic acid may suitably then be passed to a heavy ends distillation column in which propionic acid by-product is separated from dry acetic acid.

In step (VI) of the process a vapour fraction comprising methyl acetate, methyl iodide, water and acetic acid is removed from the head of the light ends distillation column.

In step (VII) of the process the overhead vapour fraction from (VI) is condensed.

In step (VIII) of the process the condensed overhead fraction from (VII) is passed to a decanter wherein the fraction is separated into an upper (aqueous) layer and a lower (organic) layer.

Finally, in step (IX) of the process the upper (aqueous) layer separated in (VIII) is recycled in whole or in part as reflux to the light ends distillation column and the lower (organic) layer separated in (VIII) is recycled in whole or in part, preferably in whole, to the reactor. The tipper (aqueous) layer is suitably returned in part to the light ends distillation column as reflux, suitably at a rate of about 0.1 to about 0.7 times the rate of removal of the vapour fraction from the head of the light ends distillation column.

BRIEF DESCRIPTION OF THE DRAWINGS

The invention will now be further illustrated by reference to the following examples and drawings in which.

EXAMPLE

Methanol was fed continuously to a carbonylation reactor in which there was maintained a liquid reaction composition comprising an iridium carbonylation catalyst, 5 wt % water, 7 wt % methyl iodide, 15 wt % methyl acetate and, comprising the remainder of the composition, acetic acid. Also fed to the reactor was carbon monoxide. The carbonylation rate was about 17.5 mol/l/hr.

Liquid reaction composition was withdrawn from the carbonylation reactor and introduced into a flash separation zone wherein a vapour fraction comprising water, acetic acid product, methyl acetate and methyl iodide and a liquid fraction comprising iridium carbonylation catalyst were produced.

The liquid fraction withdrawn from the flash separation zone was recycled to the carbonylation reactor.

The vapour fraction from the flash separation zone was introduced into a combined light ends/drying column. There was removed from the head of the combined column a vapour fraction comprising methyl acetate, methyl iodide, water and acetic acid. The vapour fraction was condensed and passed to a decanter. The combined column was operated in a manner such that acetic acid was present in the condensed overhead vapour fraction passed to the decanter in a concentration of 8 wt % or below.

In the decanter the condensed overhead vapour fraction separated into an upper (aqueous) layer and a lower (organic) layer. Upper (aqueous) layer was removed from the decanter and recycled as reflux to the combined column. Lower (organic) layer was removed from the decanter and recycled to the reactor.

A process stream comprising acetic acid product was also removed from the combined light ends/drying column.

Operation in the aforesaid manner was maintained for a period of about 18 hours.

Figure 1:
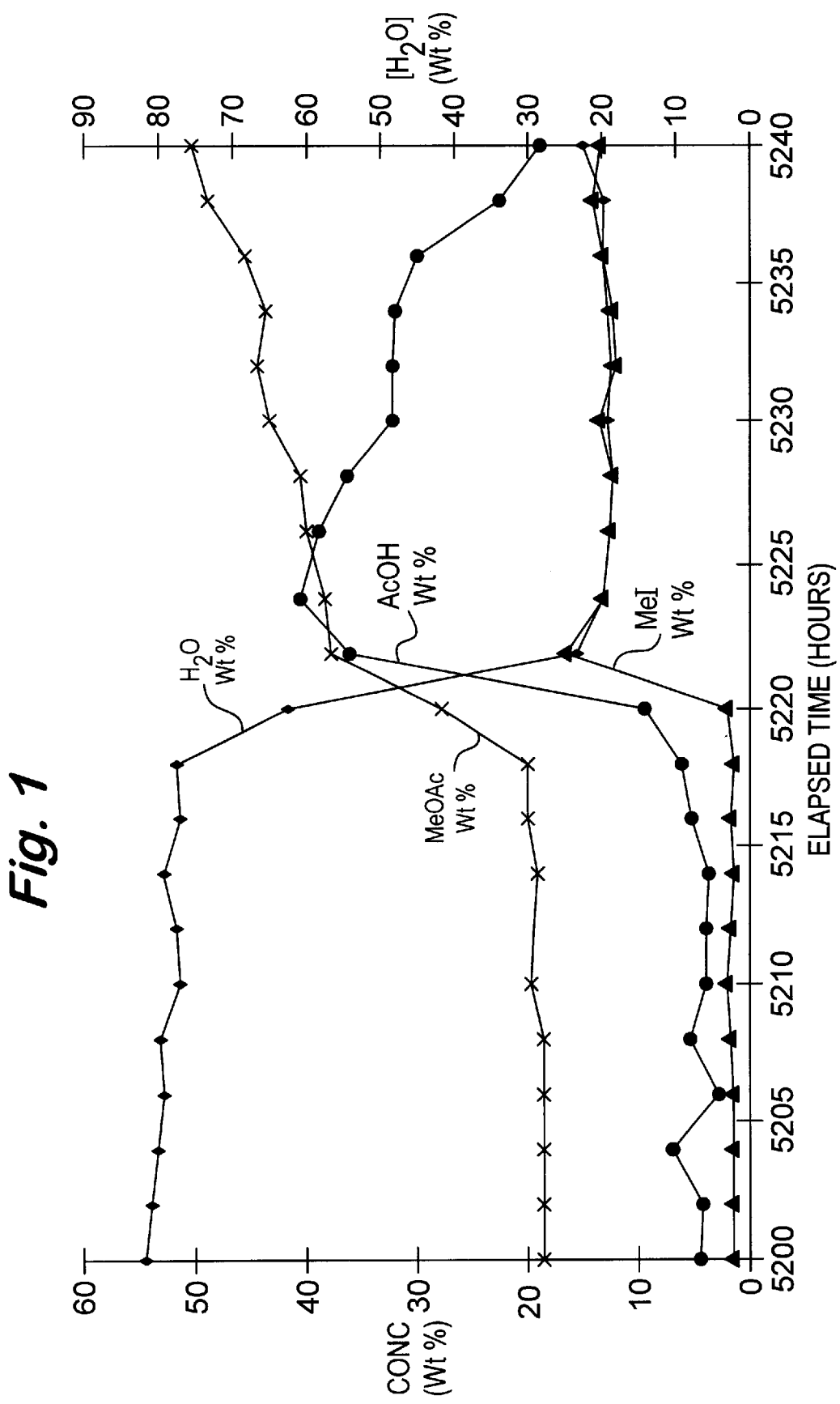
FIG. 1 is a graph of the component concentrations in the upper (aqueous) phase of the light ends overhead decanter during a continuous carbonylation process and FIG. 2 is a graph of the corresponding carbonylation rate.
Figure 2:
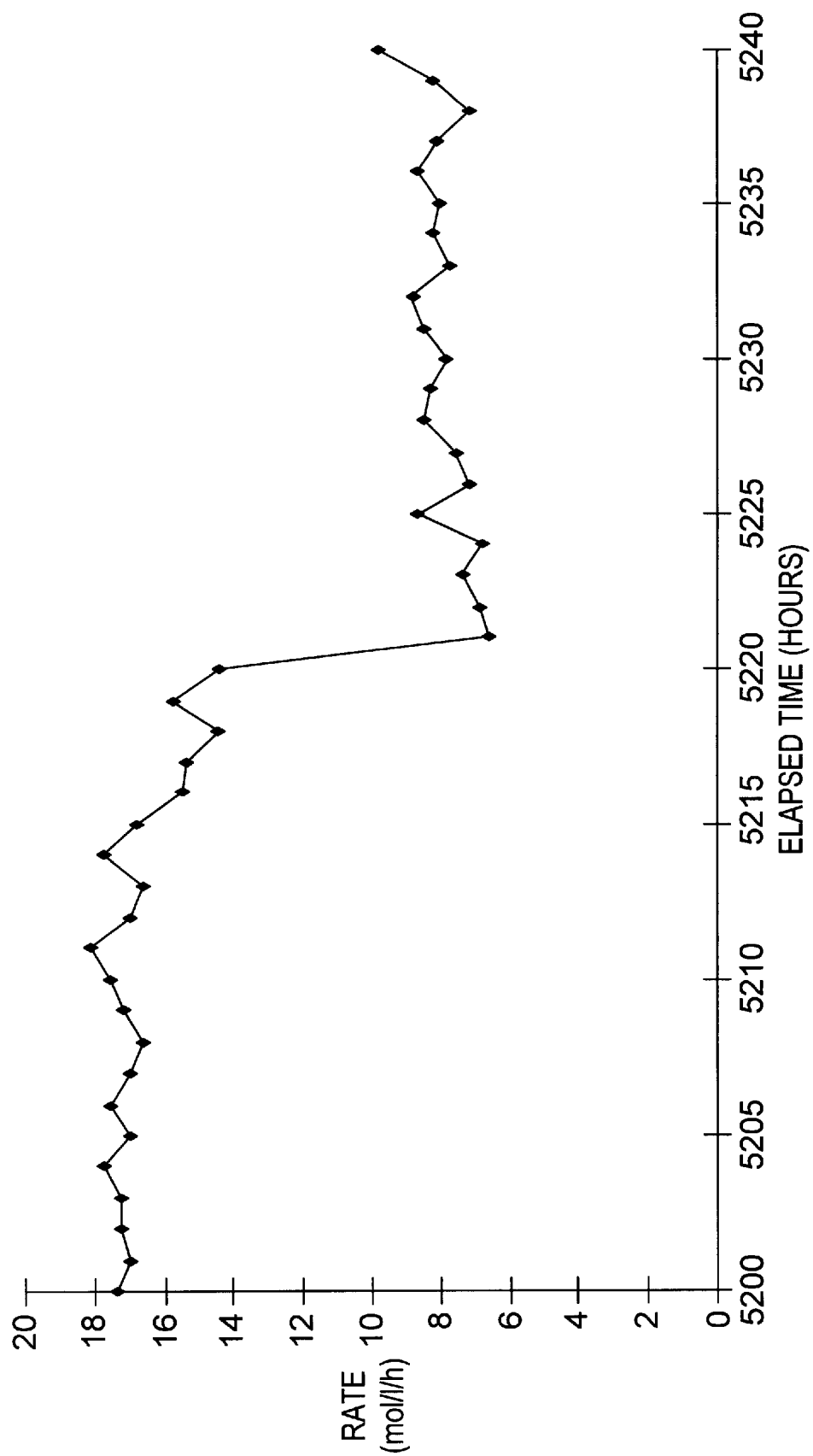

During this time stable operation of the decanter was achieved as shown in FIG. 1, which is a plot of the composition of the upper (aqueous) layer in the decanter versus time elapsed. During this period the carbonylation rate remained reasonably constant at an average value of about 17.5 mol/l/h as shown in FIG. 2, which is a plot of carbonylation rate versus time elapsed.

Comparison Test

After about 18 hours, operation of the light ends/drying column was changed in a manner such that the concentration of acetic acid in the condensed overhead vapour fraction passed to the decanter was greater than 8% w/w. This rapidly caused a change to single phase operation in the decanter with the effect on the component concentrations of the liquid in the decanter as shown in FIG. 1. It can be seen that the water concentration falls abruptly as the acetic acid concentration correspondingly increases, as does the methyl iodide and methyl acetate concentrations.

In the liquid reaction composition in the carbonylation reactor the water concentration increased to about 11 wt % and the methyl iodide concentration fell to about 3 wt % as a result of the changes in the decanter and column operating conditions. These changes were accompanied by a marked decrease in the carbonylation rate to an average value of about 8 mol/l/h to maintain a methyl acetate concentration of 15 wt % as shown in FIG. 2.

This is not an example according to the present invention and is included only for comparison purposes.

I claim:

1. In a continuous process for the production of acetic acid by the carbonylation of methanol and/or a reactive derivative thereof which process comprises the steps of:
   (I) feeding methanol and/or a reactive derivative thereof to a carbonylation reactor in which the methanol and/or reactive derivative thereof is reacted with carbon monoxide in a liquid reaction composition, the liquid reaction composition comprising a Group VIII noble metal carbonylation catalyst, methyl iodide cocatalyst at a concentration of at least 2% w/w, optionally at least one promoter, at least a finite concentration of water, methyl acetate and acetic acid product;
   (II) withdrawing liquid reaction composition from the carbonylation reactor and introducing the withdrawn liquid reaction composition into at least one flash separation zone, with or without the addition of heat, to produce a vapour fraction comprising water, acetic acid product, methyl acetate and methyl iodide, and a liquid fraction comprising Group VIII noble metal carbonylation catalyst and optionally at least one promoter;
   (III) recycling the liquid fraction from step (III) to the carbonylation reactor;
   (IV) introducing the vapour fraction from step (II) into a light ends distillation column;
   (V) removing a process stream comprising acetic acid product from the light ends distillation column;
   (VI) removing from the head of the light ends distillation column a vapour fraction comprising methyl acetate, methyl iodide, water and acetic acid;
   (VII) condensing the overhead vapour fraction from (VI);
   (VIII) passing the condensed overhead vapour fraction from (VII) to a decanter wherein the fraction is separated into an upper (aqueous) layer and a lower (organic) layer;
   (IX) recycling in whole or in part the upper (aqueous) layer separated in (VIII) as reflux to the light ends distillation column and the lower (organic) layer separated in (VIII) in whole or in part to the reactor;
   the improvement comprising maintaining the concentration of acetic acid in the condensed overhead vapour fraction passed to the decanter at or below 8 wt % while the concentration of methyl acetate present in the liquid reaction composition is at least 8% w/w, to thereby achieve separability of the upper (aqueous) layer and the lower (organic) layer in the decanter in step (VIII).

2. A process as claimed in claim 1 in which the Group VIII noble metal carbonylation catalyst comprises an iridium carbonylation catalyst.

3. A process as claimed in claim 2 in which the promoter is selected from the group consisting of ruthenium, osmium, cadmium, rhenium, mercury, gallium, indium, tungsten and mixtures thereof.

4. A process according to claim 1, 2 or 3 in which the methyl acetate concentration in the liquid reaction composition is in the range 8 to 50 wt. %.

5. A process as claimed in claim 1 in which the methyl iodide concentration in the liquid reaction composition is in the range 2 to 20% by weight, preferably in the range 4 to 16% by weight.

6. A process as claimed in claim 4 in which the methyl iodide concentration in the liquid reaction composition is in the range 2 to 20% by weight, preferably in the range 4 to 16% by weight.

7. A process as claimed in claim 1 in which the light ends distillation column has greater than 10, more preferably 15 or greater theoretical stages above the feed.

8. A process as claimed in claim 6 in which the light ends distillation column has greater than 10, more preferably 15 or greater theoretical stages above the feed.

9. A process as claimed in claim 1 in which recycle streams having a substantial acetic acid content are introduced to the light ends distillation column at a point close to the feed point of the vapour fraction from step (II).

10. A process is claimed in claim 1 in which the decanter is a bootless decanter.

11. A process as claimed in claim 1 in which the decanter contains plate pack separators.

12. A process is claimed in claim 10 in which the decanter contains plate pack separators.

13. A process according to claim 4 in which the methyl acetate concentration in the liquid reaction composition is in the range 8 to 35 wt. %.

14. A process as claimed in claim 5 in which the methyl iodide concentration in liquid reaction composition is in the range 4 to 16% by weight.

15. A process according to claim 6 in which the methyl iodide concentration in the liquid reaction composition is in the range 4 to 16% by weight.

16. A process as claimed in claim 7 in which the light ends distillation column has 15 or greater theoretical stages above the feed.

17. A process as claimed in claim 8 in which the light ends distillation column has 15 or greater theoretical stages above the feed.

* * * * *